US00PP20755P2

(12) United States Plant Patent
Larsen

(10) Patent No.: US PP20,755 P2
(45) Date of Patent: Feb. 16, 2010

(54) ***OSTEOSPERMUM* PLANT NAMED 'SUNNY FIONA'**

(50) Latin Name: *Osteospermum ecklonis*
Varietal Denomination: Sunny Fiona

(75) Inventor: Bjarne Nyholm Larsen, Odense N. (DK)

(73) Assignee: Sunny Gronnegyden APS, Odense (DK)

( * ) Notice: Subject to any disclaimer, the term of this patent is extended or adjusted under 35 U.S.C. 154(b) by 343 days.

(21) Appl. No.: 11/821,112

(22) Filed: Jun. 20, 2007

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent L Bell
(74) *Attorney, Agent, or Firm*—C. A. Whealy

(57) ABSTRACT

A new and distinct cultivar of *Osteospermum* plant named 'Sunny Fiona', characterized by its upright and mounded plant habit; freely branching growth habit; freely flowering habit; daisy-type inflorescences with oblanceolate-shaped ray florets that are initially light pink in color becoming dark pink in color with development; and good garden performance.

2 Drawing Sheets

Botanical designation: *Osteospermum ecklonis.*
Cultivar denomination: 'Sunny Fiona'.

BACKGROUND OF THE INVENTION

The present invention relates to a new and distinct cultivar of *Osteospermum* plant, botanically known as *Osteospermum ecklonis*, and hereinafter referred to by the name 'Sunny Fiona'.

The new *Osteospermum* is a product of a planned breeding program conducted by the Inventor in Odense, Denmark. The objective of the program is to create and develop new *Osteospermum* cultivars with compact and uniformly mounded plant habit, freely flowering habit and attractive inflorescence coloration.

The new *Osteospermum* originated from a cross-pollination by the Inventor in May, 2003 of a proprietary selection of *Osteospermum ecklonis* identified as code No. 50.003.02, not patented, as the female, or seed, parent with a proprietary selection of *Osteospermum ecklonis* identified as code No. 10.005.02, not patented, as the male, or pollen, parent. The new *Osteospermum* was discovered and selected by the Inventor as a single flowering plant within the progeny of the stated cross-pollination in a controlled environment in Odense, Denmark in July, 2004.

Asexual reproduction of the new *Osteospermum* by terminal cuttings in a controlled environment in Odense, Denmark since January, 2005, has shown that the unique features of this new *Osteospermum* are stable and reproduced true to type in successive generations.

SUMMARY OF THE INVENTION

The cultivar Sunny Fiona has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Fiona'.

These characteristics in combination distinguish 'Sunny Fiona' as a new and distinct cultivar of *Osteospermum:*

1. Upright and mounded plant habit.
2. Freely branching growth habit.
3. Freely flowering habit.
4. Daisy-type inflorescences with oblanceolate-shaped ray florets that are initially light pink in color becoming dark pink in color with development.
5. Good garden performance.

In side-by-side comparisons conducted in Odense, Denmark, plants of the new *Osteospermum* differ from plants of the parent selections primarily in ray floret color as plants of the female parent selection have dark purple-colored ray florets and plants of the male parent selection have white-colored ray florets.

Plants of the new *Osteospermum* can be compared to plants of the *Osteospermum* cultivar Sunny Elizabeth, disclosed in U.S. Plant Pat. No. 16,564. In side-by-side comparisons conducted in Odense, Denmark, plants of the new *Osteospermum* differed from plants of the cultivar Sunny Elizabeth primarily in ray floret color as plants of the cultivar Sunny Elizabeth had pink-colored ray florets with purple-colored stripes.

BRIEF DESCRIPTION OF THE PHOTOGRAPHS

The accompanying photographs illustrate the overall appearance of the new *Osteospermum*. This photographs shows the colors as true as it is reasonably possible to obtain in colored reproductions of this type. Colors in the photographs may differ slightly from the color values cited in the detailed botanical description which accurately describe the colors of the new *Osteospermum.*

The photograph on the first sheet comprises a side perspective view of a typical flowering plant of 'Sunny Fiona'.

The photograph at the top of the second sheet is a close-up view of a typical inflorescence of 'Sunny Fiona'.

The photograph at the bottom of the second sheet is a close-up view of the upper surface of a typical leaf of 'Sunny Fiona'.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe plants grown in De Lier, The Netherlands during the spring in a glass-covered greenhouse and under conditions and practices which approximate those generally used in commercial *Osteospermum* production. During the production of the plants, day temperatures ranged from 10° C. to 20° C., night temperatures averaged 10° C. and light levels ranged from 200 to 800 watts per square meter. Measurements and numerical values represent averages for typical flowering plants. Plants were pinched one time and were about 15 weeks old when the photographs and description were taken.

Botanical classification: *Osteospermum ecklonis* cultivar Sunny Fiona.

Parentage:

*Female, or seed, parent.*—Proprietary selection of *Osteospermum ecklonis* identified as code No. 50.003.02, not patented.

*Male, or pollen, parent.*—Proprietary selection of *Osteospermum ecklonis* identified as code No. 10.005.02, not patented.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; white in color.

*Rooting habit.*—Freely branching; moderately dense.

Plant description:

*Plant form/growth habit.*—Upright and mounded plant habit. Inflorescences positioned above the foliar plane. Low to moderately vigorous growth habit.

*Plant height.*—About 14.6 cm.

*Plant diameter.*—About 16.7 cm.

*Lateral branches.*—Quantity per plant: Freely branching, about five lateral branches per plant. Length: About 5.8 cm. Diameter: About 4.5 mm. Internode length: About 4.5 mm. Strength: Strong. Texture: Smooth, glabrous. Color: 144B.

*Foliage description.*—Arrangement: Alternate, simple; sessile. Length: About 5.9 cm. Width: About 2.9 cm. Shape: Obovate. Apex: Broadly acute to rounded. Base: Cuneate. Margin: Dentate; coarse, irregular. Texture, upper and lower surface: Smooth, glabrous; leathery; pubescent along the leaf margins. Venation pattern: Pinnate. Color: Developing foliage, upper surface: 143A. Developing foliage, lower surface: 143A to 143B. Fully expanded foliage, upper surface: Between 139A and 147A; venation, 144A to 144B. Fully expanded foliage, lower surface: 137A; venation, 144A to 144B.

Inflorescence description:

*Appearance.*—Daisy-type inflorescence form with oblanceolate-shaped ray florets. Inflorescences positioned above the foliage, arising from leaf axils. Disc and ray florets developing acropetally on a capitulum. Inflorescences face mostly upright to outward. Freely flowering habit; about 50 inflorescences develop over time per plant. Inflorescences not persistent. Inflorescences faintly fragrant.

*Flowering response.*—In northern Europe, plants of the new *Osteospermum* flower continuously from spring to late summer. Early flowering habit, plants begin flowering about eight weeks after pinching. Inflorescences last about two weeks on the plant.

*Inflorescence bud.*—Height: About 1.5 cm. Diameter: About 1.1 cm. Shape: Ovate. Color: Towards the base, 137B; towards the apex, 150B.

*Inflorescence size.*—Diameter: About 6.5 cm. Depth (height): About 1.7 cm. Disc diameter: About 4 mm. Receptacle diameter: About 9 mm. Receptacle height: About 4 mm.

*Ray florets.*—Shape: Oblanceolate. Length: About 3.2 cm. Width: About 9 mm. Apex: Retuse. Base: Attenuate. Margin: Entire. Texture: Smooth, glabrous; at the base, pubescent. Number of ray florets per inflorescence: About 24 in about two whorls. Color: When opening, upper surface: Close to 75A to 75B. When opening, lower surface: Close to 76B; towards the apex and central stripe, close to 146D. Fully opened, upper surface: Close to N74C; towards the apex, close to 73B; towards the base, close to 72A. Fully opened, lower surface: Close to 76A to 76B; towards the apex and central stripe, close to 148C to 148D.

*Disc florets.*—Shape: Tubular; apex dentate, five-pointed. Length: About 8 mm. Diameter, apex: About 3 mm. Diameter, base: About 0.9 mm. Number of disc florets per inflorescence: About 120. Color: Immature: Close to 198A to 198B; towards the apex, 116B to 116C. Mature: Apex: Close to 94B. Mid-section: Close to 77C to 77D. Base: Close to 155D.

*Phyllaries.*—Quantity per inflorescence: About 20. Length: About 9 mm. Width: About 2 mm. Shape: Lanceolate. Apex: Elongated acuminate. Base: Cuneate. Margin: Entire. Texture, upper and lower surfaces: Sparsely pubescent. Color, upper surface: 147B. Color, lower surface: 137B; towards the base, 138A.

*Peduncles.*—Length: About 5.5 cm. Diameter: About 2.5 mm. Strength: Strong. Aspect: Mostly upright to about 30° from vertical. Texture: Smooth, glabrous. Color: 144A.

*Reproductive organs.*—Androecium: Present on disc florets only. Anther shape: Narrowly oblong. Anther length: About 2 mm. Anther color: 202A. Pollen amount: Abundant. Pollen color: 21A. Gynoecium: Present on both ray and disc florets. Pistil length: About 5 mm. Stigma shape: Lanceolate. Stigma color: N186C. Style length: About 3.5 mm. Style color: N 186C. Ovary color: 145A.

*Seeds/fruits.*—Seed and fruit development have not been observed on plants of the new *Osteospermum*.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about −4° C. to about 40° C.

It is claimed:

1. A new and distinct *Osteospermum* plant named 'Sunny Fiona' as illustrated and described.

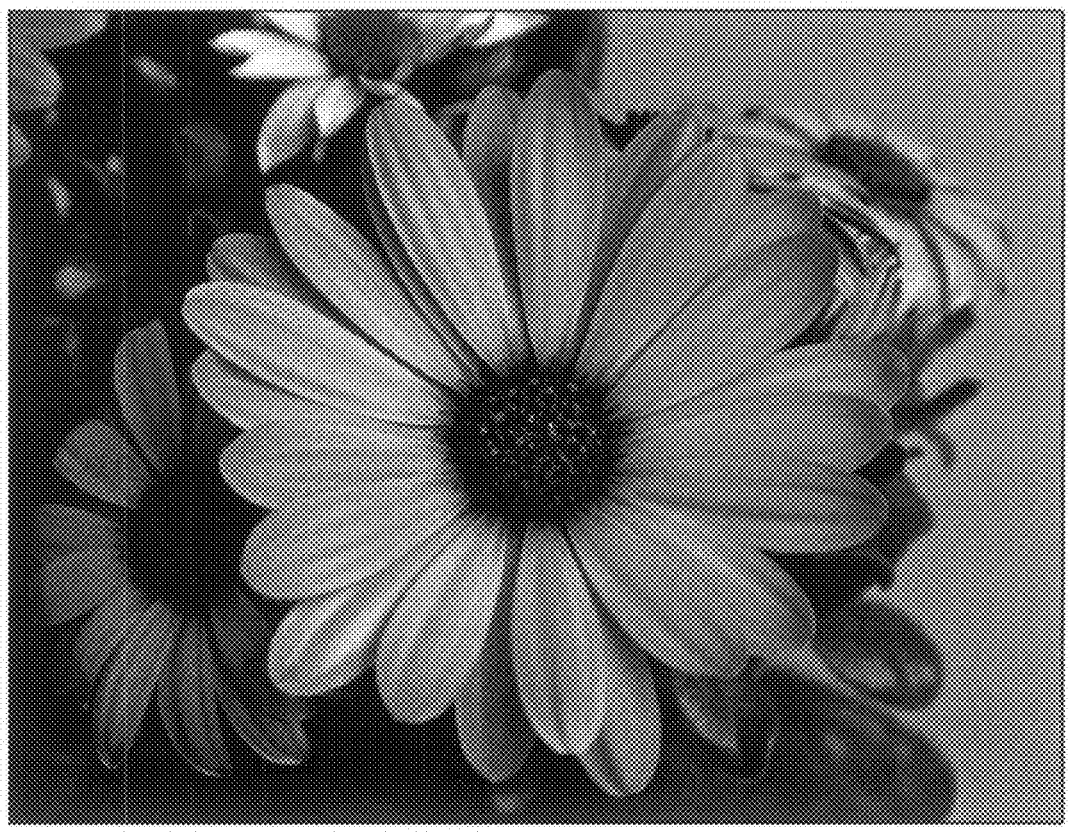
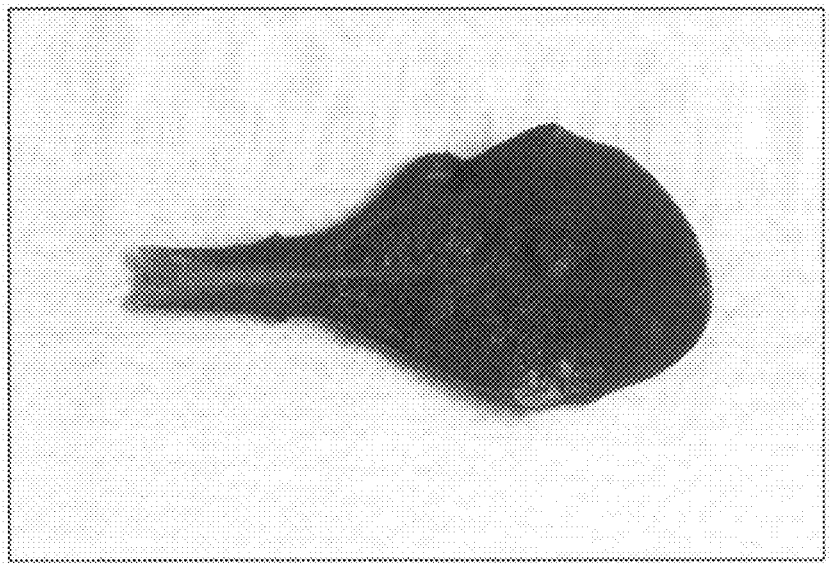

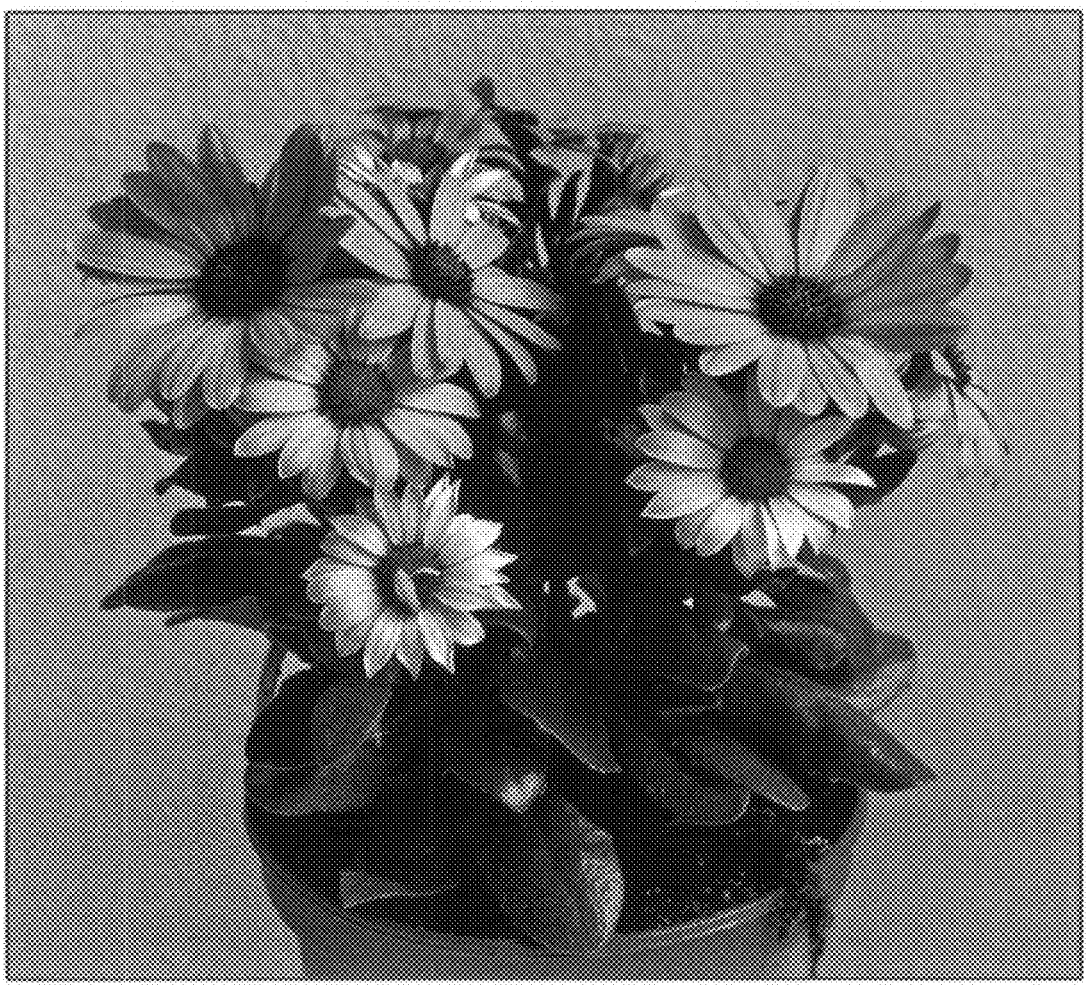

* * * * *